(12) United States Patent
Beck et al.

(10) Patent No.: US 9,057,080 B1
(45) Date of Patent: Jun. 16, 2015

(54) BIOSYNTHESIS OF STYRENE AND 7-METHYL-1,3,5-CYCLOOCTATRIENE

(75) Inventors: John J. Beck, Rocklin, CA (US); Glory B. Merrill, El Cerrito, CA (US); Jeffrey D. Palumbo, American Canyon, CA (US); Teresa L. O'Keeffe, Albany, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 919 days.

(21) Appl. No.: 12/265,264

(22) Filed: Nov. 5, 2008

(51) Int. Cl.
*C12P 7/00* (2006.01)
*C12N 1/14* (2006.01)
*C12P 5/00* (2006.01)
*C12R 1/77* (2006.01)

(52) U.S. Cl.
CPC . *C12P 5/005* (2013.01); *C12R 1/77* (2013.01); *C12P 5/002* (2013.01)

(58) Field of Classification Search
None
See application file for complete search history.

(56) References Cited

PUBLICATIONS

Vikram et al, 2005. Volatile metabolie from the headspace of onion bulbs inoculated with postharvest pathogens as a tool for disease discrimination. Canadian Journal of Plant Pathology, vol. 27(2):194-203.*
Pagot et al, 2007. Metabolism of phenylalanine and biosynthesis of styrene in *Penicillium camemberti*. Journal of Dairy Research, vol. 74:180-185; (Avalaible online Feb. 21, 2007).*
Karlshoj et al, 2007. Chapter 14. Fungal volatiles: Biomarkers of good and bad food quality. Food Mycology: A multifaceted approach to food and fungi, Editor Dijksterhuis, pp. 279-302; (Publication date: Jun. 26, 2007).*
Abdelsayed et al, 2006. Catalyzed radical polymerization of styrene vapor on nanoparticle surfaces and the incorporation of metal and metal oxide nanoparticles within polystyrene polymers. The Journal of Physical Chemistry B, col. 110:19100-19103.*
Kesselmeier and Staudt, 1999. Biogenic volatile organic compounds (VOC): An overview on emission, physiology, and ecology. Journal of Atmospheric Chemistry, vol. 33:23-88.*
Lewis et al, 1994. Soil sampling and analysis for volatile organic compounds. Environmental Monitoring and Assessment, vol. 30:213-246.*
Moller et al, 1994. Future research needs associated with the assessment of potential human health risks from exposure to toxic ambient air pollutants. Environmental Health Perspective, vol. 102(S4):193-210.*
Allcock and Lampe, 1990. Chpater 1—The Scope of Polymer Chemistry and Chapter 6—Polymerization of cyclic organic compounds. Contemporary Polymer Chemistry, pp. 12-16 and 121-122.*
Restek, Optimizing the Analysis of Volatile Organic Compounds (2003) (http://www.restek.com/pdfs/59887B.PDF).*

* cited by examiner

*Primary Examiner* — Irene Marx
(74) *Attorney, Agent, or Firm* — Elizabeth R. Sampson; John D. Fado; Lesley Shaw (57) ABSTRACT

The present invention relates to microorganisms capable of producing isolable amounts of styrene and/or 7-methyl-1,3,5-cyclooctatriene (MCOT) and uses thereof. The present invention also relates to methods for biosynthetically preparing styrene and/or 7-methyl-1,3,5-cyclooctatriene (MCOT) utilizing microorganisms capable of producing isolable amounts of styrene and/or 7-methyl-1,3,5-cyclooctatriene (MCOT).

7 Claims, 7 Drawing Sheets

BIOSYNTHESIS OF STYRENE AND 7-METHYL-1,3,5-CYCLOOCTATRIENE

FIELD OF THE INVENTION

The invention relates to biosynthetic production of styrene and 7-methyl-1,3,5-cyclooctatriene (MCOT), biosynthetically produced styrene and MCOT, microorganisms capable of producing isolable amounts of styrene and/or 7-methyl-1, 3,5-cyclooctatriene (MCOT) and uses thereof.

BACKGROUND OF THE INVENTION

Styrene, also known as vinyl benzene, is the principal monomer used in the manufacture of polystyrene plastics and resins. Many consumer products, from plastic containers to automotive parts comprise plastics and resins made from styrene. Thus, styrene is an important and essential component in the manufacture of thousands of everyday products.

In addition to the many essential products made from styrene, the styrene industry, with hundreds of companies and thousands of facilities worldwide, contributes significantly to the U.S. economy by providing thousands of well paying jobs. Indeed, according to the Styrene Information and Research Center, the styrene industry is a $28-billion industry that provides some 128,000 well-paying jobs throughout the country.

Unfortunately, 90% of styrene production is from benzene, which is a carcinogenic substance that originates from the refining of crude oil; and ethylene, which is extracted from natural gas as ethane and then steam cracked to provide ethylene. Thus current methods for styrene manufacture are highly toxic, and rely heavily on crude oil.

Crude oil is the primary feedstock for the production of fuel oil which includes gasoline, diesel, jet, heating, and other fuel oils, and liquefied petroleum gas. Thus, today, and for the foreseeable future, the primary use of crude oil is, and will be, for fuel oil and energy production. Indeed, it is estimated that by 2025 85% of the world's energy needs will be dependent upon crude oil.

Thus, the need to compete with fuel oil suppliers for limited supplies of crude oil leaves styrene manufacturers at a distinct disadvantage.

Since crude oil is vital to many industries, it can be viewed as being of importance to the maintenance of industrialized civilization itself. Thus, crude oil reserves are a critical concern to many nations and industries. At current world consumption levels, it has been estimated that known recoverable crude oil reserves could be depleted by around 2039. Thus, to maintain the quality of civilized life as we know it, in addition to energy conservation and alternative energy sources, what is needed in the art are alternative feedstock sources for production of important chemicals e.g., styrene, that are traditionally manufactured from petroleum.

Fortunately, as will be clear from the following disclosure, the present invention provides for these and other needs.

SUMMARY OF THE INVENTION

In one embodiment, the present invention provides a biosynthetic method for preparing styrene. The method comprises: (i) culturing an isolated microorganism capable of producing an isolable amount of styrene, thereby providing a microorganism culture; (ii) capturing volatile organic compounds produced by the microorganism culture thereby providing a mixture of captured volatile organic compounds; (iii) separating the captured mixture of volatile organic compounds into individual volatile organic compounds; (v) identifying styrene; and (vi) collecting the identified styrene.

In one exemplary embodiment, the isolated microorganism capable of producing an isolable amount of styrene is a filamentous fungus. In one exemplary embodiment the filamentous fungus is a member of a genus selected from the group consisting of *Cladosporium, Penicillium, Aspergillus, Fusarium, Trichoderma* and *Emericella* or a combination thereof. In one exemplary embodiment, the filamentous fungus is a *Fusarium* species. In another exemplary embodiment, the *Fusarium* species is *Fusarium oxysporum*. In still another exemplary embodiment, the *Fusarium oxysporum* is a *Fusarium oxysporum* isolated from hulls of *Prunus dulcis*. In still another exemplary embodiment, the *Fusarium oxysporum* is the *Fusarium oxysporum* assigned Accession No. NRRL 50189.

In one exemplary embodiment, the capturing volatile organic compounds produced by the microorganism culture comprises: (a) condensing volatile organic compounds produced by the microorganism culture to provide a condensate comprising a mixture of volatile organic compounds; (b) collecting the condensate thereby providing a captured mixture of volatile organic compounds; and (c) distilling the condensate to separate the mixture of volatile organic compounds into individual volatile organic compounds.

In another exemplary embodiment, the capturing volatile organic compounds produced by the microorganism culture comprises: polymerizing volatile organic compounds produced by the microorganism culture.

In still another exemplary embodiment, capturing volatile organic compounds produced by the microorganism culture comprises: (a) absorbing volatile organic compounds produced by the microorganism culture on a porous polymer absorption column, thereby providing a mixture of absorbed volatile organic compounds; and (b) desorbing the mixture of adsorbed volatile organic compounds with an appropriate solvent, thereby providing a captured mixture of volatile organic compounds. In one exemplary embodiment, the porous polymer absorption column is a Tenax column. In another exemplary embodiment, the appropriate solvent is a non-polar solvent. In one exemplary embodiment, the non-polar solvent is n-pentane.

In another exemplary embodiment, the method is practiced on an industrial scale.

In one embodiment, the present invention provides styrene prepared from a culture of an isolated microorganism capable of producing an isolable amount of styrene.

In one embodiment, the present invention provides a biosynthetic method for preparing 7-methyl-1,3,5-cyclooctatriene (MCOT), the method comprising: (i) culturing an isolated microorganism capable of producing an isolable amount of MCOT, thereby providing a microorganism culture; (ii) capturing volatile organic compounds produced by the microorganism culture thereby providing a mixture of captured volatile organic compounds; (iii) separating the captured mixture of volatile organic compounds into individual volatile organic compounds; (v) identifying MCOT; and (vi) collecting the identified MCOT.

In one exemplary embodiment, the isolated microorganism capable of producing an isolable amount of MCOT is a *Fusarium* species. In another exemplary embodiment, the *Fusarium* species is *Fusarium oxysporum*. In another exemplary embodiment, the *Fusarium oxysporum* is a *Fusarium oxysporum* isolated from hulls of *Prunus dulcis*. In another exemplary embodiment, the *Fusarium oxysporum* is *Fusarium oxysporum* assigned Accession No. NRRL 50189.

In one exemplary embodiment, capturing volatile organic compounds produced by the microorganism culture comprises: (a) condensing volatile organic compounds produced by the microorganism culture to provide a condensate comprising a mixture of volatile organic compounds; (b) collecting the condensate thereby providing a captured mixture of volatile organic compounds; and (c) distilling the condensate to separate the mixture of volatile organic compounds into individual volatile organic compounds.

In another exemplary embodiment, capturing volatile organic compounds produced by the microorganism culture comprises: polymerizing volatile organic compounds produced by the microorganism culture.

In another exemplary embodiment, capturing volatile organic compounds produced by the microorganism culture comprises: (a) absorbing volatile organic compounds produced by the microorganism culture on a porous polymer absorption column, thereby providing a mixture of absorbed volatile organic compounds; and (b) desorbing the mixture of adsorbed volatile organic compounds with an appropriate solvent, thereby providing a captured mixture of volatile organic compounds.

In one exemplary embodiment, the porous polymer absorption column is a Tenax column. In another exemplary embodiment, the appropriate solvent is a non-polar solvent. In another exemplary embodiment, the non-polar solvent is n-pentane.

In another exemplary embodiment, the method is practiced on an industrial scale.

In another embodiment, the present invention provides 7-methyl-1,3,5-cyclooctatriene (MCOT) prepared from a culture of an isolated microorganism capable of producing an isolable amount of MCOT.

In another embodiment, the present invention provides *Fusarium oxysporum* isolate assigned Accession No. NRRL 50189 or a culture therefrom.

Other features, objects and advantages of the invention will be apparent from the detailed description which follows.

DETAILED

40%, at least about 45% at least about 50% of the total volatile organic compounds produced by the microorganism. In some exemplary embodiments, a microorganism that produces an isolable amount of MCOT produces MCOT in an amount that is at least about 60%, at least about 70%, at least about 80%, or at least about 90% of the total volatile organic compounds produced by the microorganism. Thus, in general, an isolable amount of MCOT is separable and can be purified by physical means, e.g., by gas chromatography, HPLC, etc, from other VOCs produced by the microorganism.

The term "isolable" as used herein, is used in its conventional sense and refers to a chemical e.g., styrene, MCOT, etc., or microorganism capable of being isolated.

The terms "isolated," "purified" or "biologically pure" as used herein, refer to a chemical or microorganism that is substantially or essentially free from components that normally accompany it as found in its native state.

An "isolated" microorganism or population of microorganisms means an object microorganism (e.g., a *Fusarium*) is the predominant microorganism present (i.e., is more abundant than other species in the composition). In an exemplary embodiment, an isolated microorganism comprises at least about 50% of all microorganisms present. In another exemplary embodiment, an isolated microorganism comprises at least about 60% of all microorganisms present. In still other exemplary embodiments, an isolated microorganism comprises at least about 70%, at least about 80%, at least about 85%, at least about 90%, at least about 95% or at least about 99% percent of all microorganisms present.

In some exemplary embodiments, the term "isolated" is used to describe an isolated chemical compound, e.g., isolated styrene. Thus, in some exemplary embodiments, the terms "isolated" or "purified" refer to a chemical species that that is the predominant species present in a preparation. Thus, in some exemplary embodiments, "purity" of an isolated species is determined using analytical chemistry techniques such as e.g., high performance liquid chromatography. A chemical species that is the predominant species present in a preparation is substantially purified. Typically, a "purified" chemical species denotes that a chemical species that is at least about 85% pure, at least about 95% pure, or at least about 99% pure.

The expression "culture of microorganisms" as used herein refers to an in vitro population of cells. Typically, the in vitro population of cells is in culture medium such that the in vitro population of cells at least has the potential to produce a viable cell mass of cell number greater than the initial cell number. In some exemplary embodiments, a "culture of microorganisms" has grown to produce a viable cell mass of cell number greater than the initial cell number, in which case the culture can be at any stage of cell growth e.g., exponential growth (log) phase, stationary phase, etc.

The term "capture" or "capturing" as used herein, refers in the context of a biosynthetic method for preparing styrene and/or 7-methyl-1,3,5-cyclooctatriene (MCOT), to the initial step of a separation procedure for volatile organic compounds (VOCs) produced by a microorganism culture. Typically, a capture step includes collection of the VOCs produced by a microorganism culture and thus, the capture step is the first step in a purification of the volatile organic compounds away from the microorganism culture itself. In an exemplary embodiment capture of styrene and/or MCOT utilizes a sorbtion technology. In other exemplary embodiments, capture of styrene and/or MCOT utilizes condensation technology. In still other exemplary embodiments, capture of styrene utilizes polymerization from the vapor-phase.

I. Introduction

Styrene is an important chemical which is the used in the manufacture of polystyrene plastics and resins. Numerous consumer products comprise plastics and resins made from styrene. Thus, styrene is an essential component in the manufacture of thousands of everyday products. Unfortunately, styrene production must compete with the fuel oil industry for crude oil, which is the raw material required for styrene synthesis. Thus, because crude oil supplies are limited and may soon be depleted, the development of alternative feedstocks for styrene productions is needed in the art.

Fortunately, the present inventors have now discovered that styrene and other important chemical products e.g., MCOT, can be produced biosynthetically. Therefore, in one exemplary embodiment, the invention provides a biosynthetic method for preparing styrene. The method comprises: (i) culturing an isolated microorganism capable of producing an isolable amount of styrene, thereby providing a microorganism culture; (ii) capturing volatile organic compounds produced by the microorganism culture thereby providing a mixture of captured volatile organic compounds; (iii) separating the captured mixture of volatile organic compounds into individual volatile organic compounds; (v) identifying styrene; and (vi) collecting the identified styrene.

In other exemplary embodiments the invention provides a biosynthetic method for preparing 7-methyl-1,3,5-cyclooctatriene (MCOT), styrene and MCOT made by biosynthetic methods and an isolated *Fusarium oxysporum* species capable of producing isolable amounts of styrene and/or MCOT.

Although it is known that certain microorganisms produce styrene under some conditions (see e.g., S. E. Pinches and P. Apps (2007) *Int. J. of Food Microbiology* 116(1): 182-185; Nieminen, T., et al. (2008). *LWT—Food Sci. Technol.* 41:2051; Pagot, Y., et al. (2007) *J. Dairy Res.* 74: 180-185), it has not heretofore been appreciated that microorganisms can be used for biosynthetic production of styrene and other important industrial chemicals.

II. Microorganisms Capable of Producing an Isolable Amount of Styrene and/or 7-Methyl-1,3,5-Cyclooctatriene (MCOT)

A. General Methods

Methods disclosed herein utilize routine techniques in the field of microbiology. Basic texts disclosing the general methods of use in this invention include, e.g., *Accessing Uncultivated Microorganisms from the Environment to Organisms and Genomes and Back*; Karsten Zengler, ed. ASM Press (2008); *Methods for General and Molecular Microbiology*, 3rd Edition, C. A. Reddy, et al., eds. ASM Press (2008); and *Encyclopedia of Microbiology*, 2nd ed., Joshua Lederburg, ed., Academic Press (2000).

Methods disclosed herein also utilize routine techniques in the field of molecular biology. Basic texts disclosing the general methods of use in molecular biology include e.g., Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)).

Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise noted, technical terms are used according to conventional usage. Definitions of common terms in microbiology maybe found in e.g., *Microbiology* By Cliffs Notes, I. Edward Alcamo, Wiley (1996); Encyclopedia of Microbiology, (2000) supra; Singleton et al., Dictionary of Microbiology and Molecular Biology (2d ed. 1994). Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

B. Features of Microorganisms Capable of Producing Isolable Amounts of Styrene and/or 7-methyl-1,3,5-cyclooctatriene (MCOT)

Any microorganism capable of producing an isolable amount of styrene and/or 7-methyl-1,3,5-cyclooctatriene (MCOT) is useful in the methods disclosed herein. In one exemplary embodiment, a microorganism capable of producing an isolable amount of styrene and/or 7-methyl-1,3,5-cyclooctatriene (MCOT) is a filamentous fungus. In another exemplary embodiment, the filamentous fungus is a member of a genus selected from the group consisting of *Cladosporium, Penicillium, Aspergillus, Fusarium, Trichoderma* and *Emericella*. In another exemplary embodiment, a microorganism capable of producing an isolable amount of styrene and/or 7-methyl-1,3,5-cyclooctatriene (MCOT) is of the genus *Fusarium*. In another exemplary embodiment, a microorganism capable of producing an isolable amount of styrene is of the genus *Pennicillium*.

Volatile Organic Compound (VOC) Sampling and Analysis

In an exemplary embodiment, volatile organic compounds (VOCs) produced by a culture of microorganisms, are subjected to analyses to determine if the composition and amount of the VOCs is indicative of a microorganism culture that comprises a microorganism capable of producing an isolable amount of styrene and/or 7-methyl-1,3,5-cyclooctatriene (MCOT).

Any suitable method for sampling VOCs from a culture or a collection of microorganisms may be used. Exemplary sampling methods include, but are not limited to the use of sorbent sampling tubes e.g., charcoal tubes, Tenax tubes, SPME fibers and XAD2 tubes. Sorbent sampling is well known in the art (see e.g., ASTM D6196-03 Standard Practice for Selection of Sorbents, Sampling, and Thermal Desorption Analysis Procedures for Volatile Organic Compounds in Air; I. Ciucanu et al. (2003) *Anal. Chem.,* 75 (4):736-741; Harper, M. (2000) Journal of Chromatography A 885 (1-2):129-151; EPA Method 5021A: *Volatile Organic Compounds in Various Sample Matrices Using Equilibrium Headspace Analysis*).

Sampled VOCs are then analyzed to determine whether the microorganisms in the culture are capable of producing isolable amounts of styrene and/or MCOT. In some exemplary embodiments, the analytic/determinative method is carried out using an instrument, e.g., a gas chromatograph, and the analytic instrument is coupled to the sampling device. Exemplary analytical/determinative methods include, but are not limited to: gas chromatography (GC); gas chromatography-mass spectrometry (GC-MS) (see e.g., Beck, J. J.; et al. (2008) *J. Sci. Food. Agric.* 2008, 88, 1363-1368).

Thus, the skilled artisan, having access to this disclosure and the knowledge of the art, will recognize appropriate sampling and analytical methods for their particular experiment. Having chosen appropriate sampling and analytical methods the skilled artisan is prepared to sample VOCs produced by a microorganism culture, to determine if the microorganism culture comprises microorganisms capable of producing an isolable amount of styrene and/or MCOT. Any number of samples and any sampling interval can be used, provided that the number of samples and/or the sampling interval permit the skilled artisan to determine that the amount of styrene and/or MCOT is large enough relative to other volatile organic compounds (VOCs) produced by the microorganism to be identified and purified away from the other VOCs.

In some exemplary embodiments, a microorganism capable of producing isolable amounts of styrene and/or MCOT, produces isolable amounts of styrene and/or MCOT at different times in the growth cycle. In an exemplary embodiment, a microorganism culture is sampled over time in order to determine if microorganisms comprising the culture are capable of producing an isolable amount of styrene and/or MCOT. Indeed, in some exemplary embodiments a culture of microorganisms capable of producing an isolable amount of styrene and/or MCOT, produces only styrene early in its growth/production cycle. In other exemplary embodiments, a culture of microorganisms capable of producing an isolable amount of styrene and/or MCOT, produces only styrene. In still other exemplary embodiments, a culture of microorganisms capable of producing an isolable amount of styrene and/or MCOT, produces only styrene early in its growth/production cycle and later produces an isolable amount of MCOT. In still other exemplary embodiments, a culture of microorganisms capable of producing an isolable amount of styrene and/or MCOT, produces only MCOT. In some exemplary embodiments, styrene and MCOT are produced at the same time in the growth/production cycle. In other exemplary embodiments, styrene and MCOT are produced at different times in the growth/production cycle.

In general, microorganisms are inoculated onto a small volume of the appropriate growth media. The cultures are allowed to grow over a suitable time period, typically for at least about seven days under standard growing conditions. As the skilled artisan will readily appreciate, cells in log phase typically provide the bulk of production of end product e.g., styrene, MCOT. The skilled artisan also appreciates that growth periods vary in accordance with the temperature at which the culture is grown and with the nature of the growth medium. Typically, within the normal temperature for growth, warmer temperatures provide for faster growth rates, and richer growth medium provides for faster growing and/or denser cultures. After a suitable time period, flasks are tightly sealed for at least about 1 min and the VOCs are captured e.g., using SPME, and analyzed e.g., using GC-MS.

In some exemplary embodiments, the culture of microorganisms is a mixed culture, e.g., comprises more than one species of microorganism (see e.g., Taniguchi, M., (2004) Adv, in Biochem. Eng. Biotech. 90:35-62). In one exemplary embodiment, the mixed culture is a fungal bouquet from almond hulls. In other exemplary embodiments, the culture of microorganisms is a pure culture of a single microorganism strain, e.g., a culture of purified *Fusarium oxysporum*.

C. Methods for the Isolation and Cultivation of Microorganisms Capable of Producing Isolable Amounts of Styrene and/or 7-methyl-1,3,5-cyclooctatriene (MCOT)

Microorganisms capable of producing an isolable amount of styrene and/or MCOT can be isolated and purified using any of a variety of methods known to those of skill in the art which may be used for isolation of microorganisms (see e.g., *Accessing Uncultivated Microorganisms from the Environment to Organisms and Genomes and Back*, supra; *Methods for General and Molecular Microbiology*, 3rd Edition, supra.

Microorganisms can be obtained from almost any source, e.g., soil samples, husks from *Prunus dulcis*, vertebrate digestive systems etc, suspected of comprising microorganisms capable of producing isolable amounts of styrene and/or MCOT. Once a sample is identified and obtained microorganisms are cultivated using standard microbial cultivation techniques which are well known in the art (see e.g., E Y. Park (2004) Recent Progress in Microbial Cultivation Techniques, In: *Advances in Biochemical Engineering/Biotechnology* vol. 90:1-33).

In an exemplary embodiment, pure cultures of a single microorganism are obtained by isolating single colonies from a streak plate. Colony streaking is a well known method for the isolation of individual cells and subsequently for the production of a pure culture. As is well known in the art, a streak plate is prepared by spreading a microbial inoculum back and forth with an incoluating loop over the solid agar plate. Upon incubation, colonies will arise and single cells will have been isolated from the biomass.

In an exemplary embodiment, *Fusarium* species are isolated from a soil sample (see e.g., Bragulat, M. R., et al. (2004) Journal of food protection 67(1): 207-211). In another exemplary embodiment *Fusarium* species are isolated from husks of *Prunus Dulcis* (see e.g., Example 1).

In another exemplary embodiment *Penicillium* species are isolated from husks of *Prunus Dulcis* (see e.g., Example 2).

Although standard microbial cultivation techniques are typically used other methods known to those of skill in the art can be used to isolate microorganisms capable of producing isolable amounts of styrene and/or MCOT (see e.g., U.S. Pat. No. 7,008,767)

While it is not critical to practice of the methods for biosynthetic production of styrene and/or MCOT as disclosed herein, once a pure culture of a microorganism capable of producing isolable amounts of styrene and/or MCOT has been obtained, the microorganism can be identified, if identification is desired.

In an exemplary embodiment, a microorganism capable of producing isolable amounts of styrene and/or MCOT is identified from analysis of nuclear large subunit (26S) ribosomal DNA by methods known in the art (see e.g., Kurtzman, C. P., et al. (1998) (*Antonie Van Leeuwenhoek* 73: 331-371 and Example 1). However, any suitable microbial identification technique may be used (see e.g., Plaza, G. A., et al. (1997) *Pol. J. Environ. Stud.* 13: 315-318; Amann, R. I., et al. (1990) Appl Environ Microbiol. 56(6): 1919-1925).

Media and Carbon Substrates

Growth of a microorganism selected for use in the methods disclosed herein may be achieved by one of ordinary skill in the art by the use of appropriate nutrient medium. Appropriate media for the growing of microorganisms capable of producing an isolable amount of styrene and/or MCOT include those that provide nutrients necessary for the growth of microbial cells. See e.g., *Methods for General and Molecular Microbiology*, 3rd Edition, C. A. Reddy, et al., eds. ASM Press (2008); *Media Design for Industrial Fermentations, Nutritional Requirements of Commercially Important Microorganism*, T. W. Nagodawithana and G. Reed, eds. Esteekay Associates, Inc., Milwaukee, Wis., 18-45 (1998); *Manual of Industrial Microbiology and Biotechnology*, A. L. Demain and N. A. Solomon, eds. American Society for Microbiology, Washington, D.C., 122-136 (1986). A typical medium for growth includes necessary carbon sources, nitrogen sources, and trace elements. Inducers e.g., glucose, may also be added to the medium. The term inducer as used herein, includes any compound enhancing formation of either styrene or MCOT by the microbial cell. In one exemplary embodiment, glucose is added to the culture medium to prolong and/or enhance the production of styrene. In other exemplary embodiments, propylene glycol, glycerol and/or 1,3-propanediol are added to the culture medium to prolong and/or enhance the production of styrene.

Exemplary carbon sources include sugars e.g., glucose, fructose, galactose, maltose, sucrose, mannitol, sorbital, glycerol, starch, etc; organic acids e.g., sodium acetate, sodium citrate, etc; alcohols e.g., ethanol, propanol and the like.

Exemplary nitrogen sources include an N-Z amine A, corn steeped liquor, soybean meal, beef extract, yeast extract, tryptone, peptone, cottonseed meal, peanut meal, amino acids e.g., sodium glutamate, etc, sodium nitrate, ammonium sulfate and the like.

Exemplary trace elements include magnesium, manganese, calcium, cobalt, nickel, iron, sodium and/or potassium salts. In some exemplary embodiments, phosphates may also be added in trace or greater than trace amounts.

In some exemplary embodiments, the medium employed for growth of a microorganism capable of producing an isolable amount of styrene and/or MCOT in small scale culture or in a larger fermentation includes more than one carbon or nitrogen source or other nutrient.

In other exemplary embodiments medium for growth includes aqueous media, particularly that which is described in the Examples herein. Other defined or synthetic growth media may also be used and the appropriate medium for growth of the particular microorganism will be known by someone skilled in the art of microbiology or fermentation science.

Culture Conditions

In general, growth and culturing of a microorganism capable of producing an isolable amount of styrene and/or MCOT according to the methods disclosed herein is adjusted by the skilled artisan to accommodate the microorganism in culture.

Typically, growth temperatures are in a range that is between about 24° C. and about 37° C. The skilled artisan will be able to determine which temperature is suitable for optimal culture growth. In an exemplary embodiment, the cultured microorganism is a *Fusarium* species which is grown at a temperature that is in a range that is between about 24° C. and about 37° C. In one exemplary embodiment, the cultured microorganism is *Fusarium oxysporum* which is grown at a temperature that is in a range that is between about 24° C. to about 37° C. In one exemplary embodiment, the *Fusarium oxysporum* is grown at a temperature of about 22° C. In one exemplary embodiment, the cultured microorganism is *Fusarium oxysporum* which is grown temperature of about 27° C. In another exemplary embodiment, the cultured microorganism is a *Penicillium* species which is grown at a temperature that is a range that is between about 20° C. to about 32° C. In one exemplary embodiment, the cultured microorganism is a *Penicillium* species which is grown at a temperature of about 26° C.

In general, for the growth of microorganisms capable of producing an isolable amount of styrene and/or MCOT the pH of the medium is typically from about 5 to about 8 the precise pH for a particular microorganism is readily selected by a person having ordinary skill in the art by referring to any general text in microbiology. See e.g., *Methods for General and Molecular Microbiology*, 3rd Edition, C. A. Reddy, et al., eds. ASM Press (2008).

III. Capture of Volatile Organic Compounds (VOC) Produced by Microorganisms Capable of Producing Isolable Amounts of Styrene and/or 7-Methyl-1,3,5-Cyclooctatriene (MCOT)

Volatile organic compounds produced by a microorganism culture are captured by any convenient method known in the art. A person having skill in the art will be able to assess the factors that influence their choice of method e.g., desired scale of isolation, available equipment, etc, and will be able to recognize the method most suitable to their needs.

Figure 1:
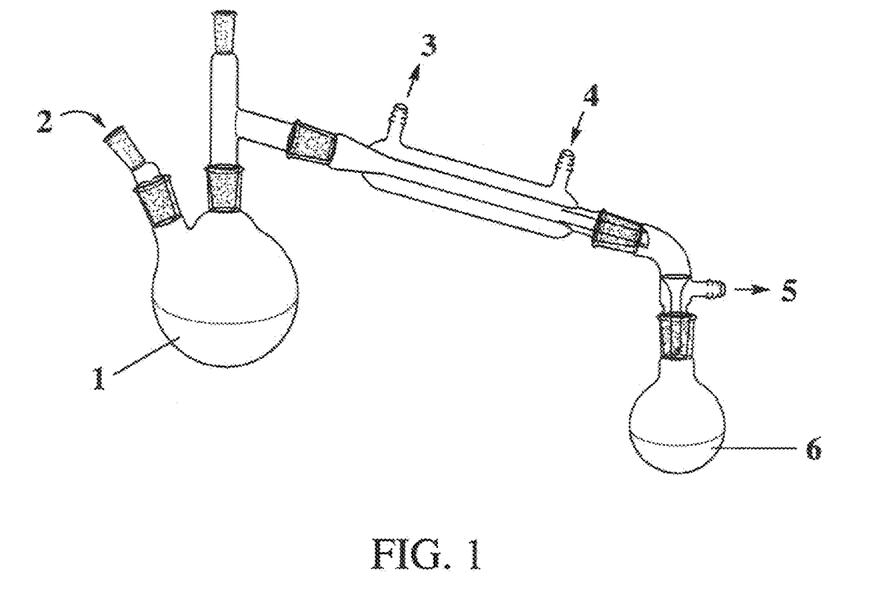
FIG. 1 Schematic of capturing of VOCs as their liquid form, after condensation: 1. Flask containing styrene-producing fungus in PDB; 2. Stream of purified air; 3. Coolant out; 4. Coolant in; 5. Slight vacuum to facilitate removal of VOCs over PDB; 6. Collected styrene and/or MCOT with polymerization inhibitor present.

In an exemplary embodiment, VOCs are captured using sorbent technology. Sorbent capture is well known in the art (see e.g., ASTM D6196-03 supra; I. Ciucanu et al. (2003) supra; Harper, M. (2000) supra; EPA Method 5021A: *Volatile Organic Compounds in Various Sample Matrices Using Equilibrium Headspace Analysis*; U.S. Pat. No. 5,595,586). In another exemplary embodiment, volatile organic compounds (VOCs) produced by a microorganism culture are captured and condensed as liquids and are subsequently separated by distillation. Thus, in an exemplary embodiment, a flask or other appropriate container comprising growth medium inoculated with microorganisms capable of producing an isolable amount of styrene and/or MCOT is heated to a temperature that is in a range that is between about 25° C. to about 37° C. The flask is connected to a distillation apparatus FIG. 1, and a source of purified air flowing at a controlled rate (e.g., 6 mL/min). The VOCs are condensed as they pass through a jacketed condensing tube, wherein the jacket has a coolant running through it. A slight vacuum is applied at the vacuum adapter to facilitate the removal of VOCs over the PDB. The collection flask contains a polymerization inhibitor e.g., 2-methylbenzoquinone-4-oxime, quinone alkides (see e.g., U.S. Pat. No. 4,237,326, U.S. Pat. No. 4,003,800 U.S. Pat. No. 5,910,232), and is kept at a temperature at or below 0° C. Once collected, the condensed styrene and/or MCOT are distilled via known methods (see e.g., U.S. Pat. No. 4,959,128, U.S. Pat. No. 4,033,829, U.S. Pat. No. 5,386,075).

Figure 2:
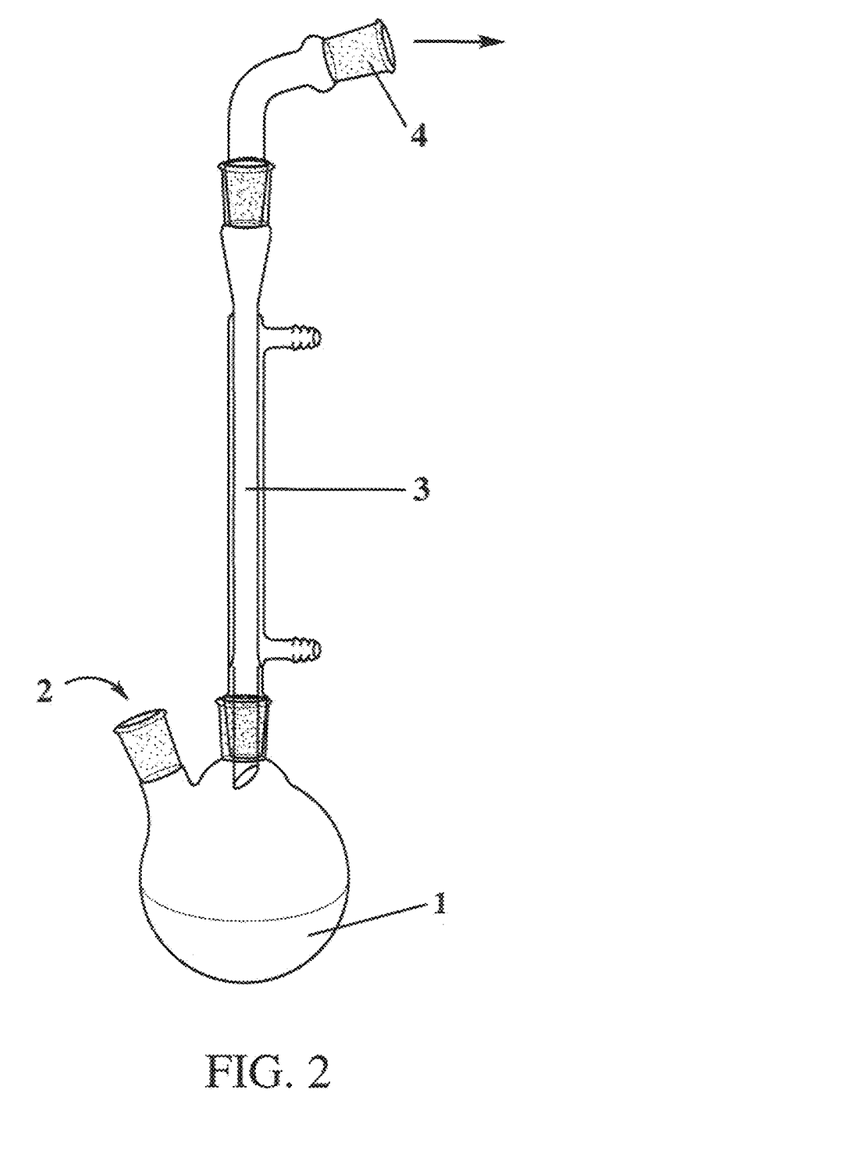
FIG. 2 Schematic of capturing and polymerizing styrene as it is emitted from the inoculated PDB: 1. Flask containing styrene-producing fungus in PDB; 2. Stream of purified air; 3. Modified distillation tube; 4. Effluent tube for directing leftover VOCs.

In another exemplary embodiment, styrene is captured and separated by polymerization in the vapor-phase as it is generated by the culture of microorganisms. Thus, in an exemplary embodiment, a flask or other appropriate container comprising growth medium inoculated with microorganisms capable of producing an isolable amount of styrene, is heated to a temperature in a range that is between about room-temperature to about 37° C., is connected to a modified distillation tube (see FIG. 2). The modified distillation tube is lined with a suitable catalyst for polymerization of vapor-phase styrene (see e.g., Kantam, M. L., et al. (2005) *J. Mol. Cat. A*. 240: 103-108; Abdelsayed, V., et al. (2006) *J. Phys. Chem. B* 110: 19100-19103) and is heated to an appropriate polymerization temperature. The modified distillation tube is capped with an effluent tube that directs remaining VOCs to an appropriate container.

In some exemplary embodiments, styrene is extracted from the growth medium. In an exemplary embodiment, styrene is extracted from the growth medium after completion of VOC collection. Media comprising the microorganisms capable of producing an isolable mount of styrene is vacuum-filtered to remove the microorganisms e.g., through a fritted-filter, to provide clarified media. The clarified media is extracted using an organic solvent e.g., n-pentane, diethyl ether by methods known in the art (see e.g., *J. Agric. Food Chem.* 2008, 56, 5062-5068, or *J. Agric. Food Chem.* 2007, 55, 6977-6983). The combined organic solvent comprising styrene is subjected to separation and isolation techniques via known methods (e.g., GC-MS, HPLC).

IV. Identification and Separation of Mixtures of Volatile Organic Compounds (VOCS)

Styrene and/or MCOT can be identified and separated from other VOCs using any method known in the art. Exemplary identification/separation methods include, but are not limited to gas chromatography (GC), gas chromatography-mass spectrometry (GC-MS), high performance liquid chromatography (HPLC) all of which are well known in the art (see e.g., Lloyd R. Snyder and John W. Dolan (2006). *High-Performance Gradient Elution: The Practical Application of the Linear-Solvent-Strength Model*. Wiley Interscience; Message, Gordon M. (1984). *Practical aspects of gas chromatography/mass spectrometry*. New York: Wiley; Adlard, E. R.; Handley, Alan J. (2001). *Gas chromatographic techniques and applications*. London: Sheffield Academic).

V. Industrial Scale Production

Batch and Continuous Fermentations

In exemplary embodiments, biosynthetic methods for the production of styrene and/or MCOT are carried out on an industrial scale.

Generally, to scale up a method for cultivating a microorganism capable of producing isolable amounts of styrene and/or MCOT for industrial scale production, the culture of microorganisms is scaled up first to pilot scale (e.g., 0.07, 0.8, 19 $m^3$) and then to production scale (e.g., 57 $m^3$). In one exemplary embodiment, the microorganism capable of producing isolable amounts of styrene which is scaled up for industrial production is *Fusarium oxysporum*. In another exemplary embodiment, the microorganism capable of producing isolable amounts of styrene which is scaled up for industrial production, is *Fusarium oxysporum* having Accession No. NRRL 50189.

As the skilled artisan will appreciate, significant numbers of fermentations are needed under varying environmental and nutritional conditions to find optimal conditions for scaling up of a particular bioprocess.

Optimization typically begins with shake flasks experiments and is then scaled to in 1- to 100-liter laboratory scale bioreactors (see e.g., Hebbar, K. P., et al. (1997) *Appl. Microbiol. Biotechnol.* 48: 714-719; Tholudur, A. et al., Biotechnol. Bioeng. 66: 1 16 (1999)). To decrease the number of experiments required for optimization, mathematical modeling may be used (see e.g., Alvarez-Ramirez, J. et al., J. Chem. Technol. Biotechnol. 74: 78 84 (1999); Boon, M. A. et al., Biotechnol Bioeng. 64: 558 567 (1999); Cooney, M. J. et al., Biotechnol. Prog. 15: 898 910 (1999); Tholudur A. et al., Biotechnol. Bioeng. 66: 1 16 (1999)).

Scale-up for the growth of microorganisms is usually based on maintaining a constant dissolved oxygen concentration in the liquid (broth), independent of reactor size. Additionally, temperature, pressure, pH, and flow rate must be kept at very specific levels to ensure optimum culture growth, and thus optimum production of product e.g., styrene (see e.g., T. J. Bailey and D. Ollis, *Biochemical Engineering*, 2nd ed., McGraw-Hill, New York, 1987; D. W. Hubbard, L. R. Harris, and M. K. Wierenga, *Chem. Eng. Prog.*, 84 (8), p. 55 (1988); D. C. Wang et al., *Fermentation and Enzyme Technology*, Wiley, New York, (1979); H. Scott Fogler, *Elements of Chemical Kinetics and Reactor Calculations*, Prentice-Hall, New Jersey, (1974); Encyclopedia of Bioprocess Technology, Flickinger, M. C., and Drew, S. W. eds. John Wiley & Sons (2008)).

As is well known in the art, scale-up of a mixing process in fermentation can be broken down into individual, interrelated steps (see e.g., Oldshue, J. Y. (1966) Biotechnol. Bioeng. 8: 3-24). Thereby allowing consideration of the effect of mixing on gas-liquid absorption, fluid shear rates, blending, and heat transfer to be evaluated separately. Since a bioreactor is three-dimensional, one of skill in the art will appreciate the importance of remembering that as the linear dimensions increase, the capacity of the system increases as the cube of the linear dimension. With this increase in scale, other variables rise on the linear scale with different exponents, which may vary from negative to zero to three and higher.

Other factors to consider include, but are not limited to: control of shear stress which, if too great, can cause lysis of cells in culture. Consequently, scale-up and thorough mixing of cells, nutrients, and oxygen need to be carefully balanced. In addition, cells can aggregate, which poses the problems of maintaining a supply of nutrients and removal of wastes.

The skilled artisan having access to this disclosure and the knowledge in the art will be able to determine and optimize a large scale fermentation process for use with the methods disclosed herein. In an exemplary embodiment, the process employs a batch method of fermentation (see e.g., Cinar, A., et al. (2003) *Batch Fermentation: Modeling, Monitoring, and Control* CRC Press). In another exemplary embodiment, the process employs a continuous fermentation process (see e.g., U.S. Pat. No. 4,748,123; Karkare, S. B. et al. (1985) *Bio/Technology* 3, 247-251).

VI. Deposit Information

A deposit of the *Fusarium oxysporum* strain I3-8 disclosed hereinbelow and recited in the appended claims has been made with the Agricultural Research Service Culture Collection (NRRL), National Center for Agricultural Utilization Research, Agricultural Research Service, U.S. Department of Agriculture, 1815 North University Street, Peoria, Ill. 61604 U.S.A. The date of deposit was Oct. 23, 2008. All restrictions upon the deposit have been removed, and the deposit is intended to meet all of the requirements of 37 C.F.R. 1.801-1.809. The NRRL accession number is 50189. The deposit will be maintained in the depository for a period of 30 years, or 5 years after the last request, or for the effective life of the patent, whichever is longer, and will be replaced as necessary during that period.

The following examples are offered to illustrate, but not to limit the invention.

EXAMPLES

Example 1

The following example illustrates the isolation and identification of styrene-producing fungal strains.

Almonds that underwent previous VOC analysis (see e.g., Beck, J. J, et al. (2008). *J. Sci. Food. Agric.* 88: 1363-1368) were sliced into quarters and allowed to stand in their 12 L collection flask to accumulate fungi on their surfaces; ambient volatiles were directed into the appropriate effluent hood. The volatiles emitted were occasionally monitored for VOC composition using SPME and GC-MS for VOC collection and identification by methods known in the art (see e.g., Beck, J. J. et al., (2008) *J. Agric. Food Chem.* 2008, 56, 2759-2764).

Fungi were isolated from the hulls of insect-damaged or mechanically damaged almonds on which visible fungal growth was present. Almonds were washed individually in 25 mL of 0.05% Tween 80, 30% glycerol by vortexing for 30 seconds in 50 mL conical tubes, and stored at $-20°$ C. Almond washes were inoculated onto potato dextrose agar (PDA) for cultivation of fungal populations.

For the analysis of volatile compounds produced by these fungal populations, almond washes (100 µL each) were inoculated into 25 mL screw-top Erlenmeyer flasks containing 10 mL of PDA and fitted with Teflon-lined septum screw caps. Cultures were incubated at $28°$ C. for 6 days with the screw caps loosened to allow for air exchange. Caps were then tightened to seal the flasks, and cultures were incubated for 24 h at $28°$ C. to allow for accumulation of volatile compounds in the flask headspace.

From fungal populations (mixed cultures) that produced styrene, individual fungal colonies were isolated by spreading 100 µL of the corresponding almond wash onto PDA supplemented with 100 mg/L chloramphenicol and incubated for 2 days at $28°$ C. Random colonies were transferred to individual PDA plates and incubated at $28°$ C. for 7 days to ensure culture purity. Pure cultures of individual fungal isolates were inoculated onto PDA in 25 mL screw-top Erlenmeyer flasks and incubated as described above. Three fungal isolates produced styrene under these conditions, and were designated I3-4, I3-5, and I3-8. Strain I3-8 is deposited as Accession No. NRRL 50189.

Figure 3A:
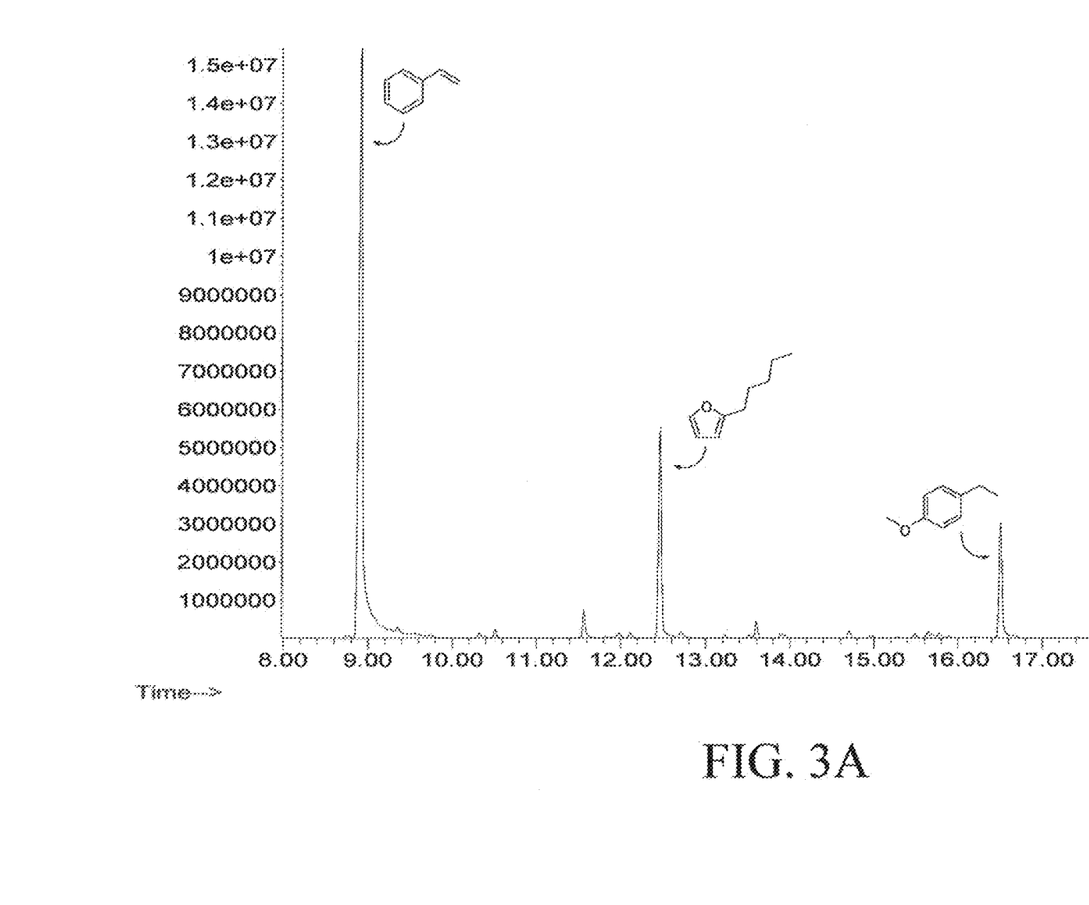
FIG. 3 GC traces of VOCs from A, fungal bouquet on almonds; B, fungal bouquet on PDA; and C, isolated fungus *F. oxysporum* strain on PDA FIG. 4. Graph of styrene and MCOT production from *F. oxysporum* grown on PDA over 12 days, small scale. Samples were monitored for styrene every 24 h by SPME.
Figure 3B:
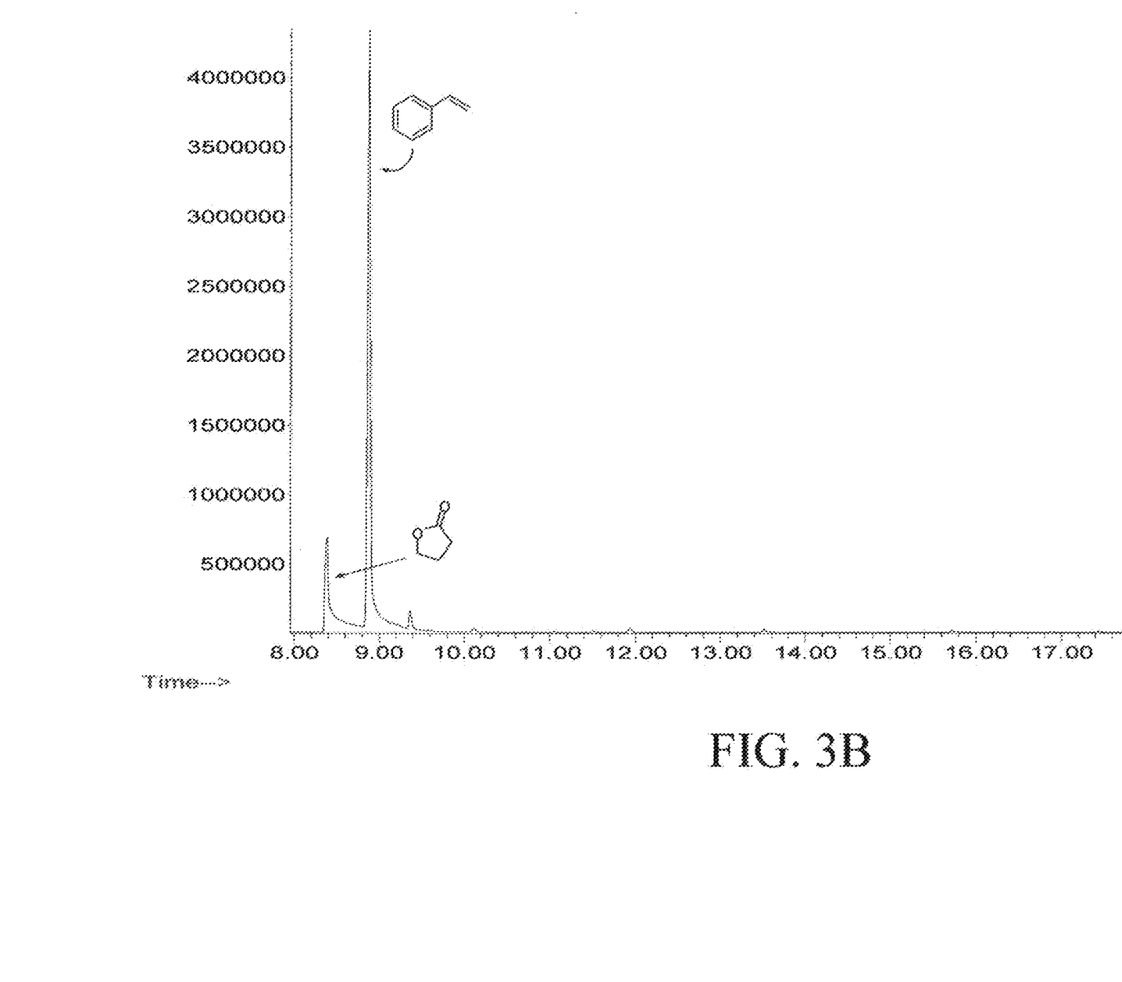
Figure 3C:
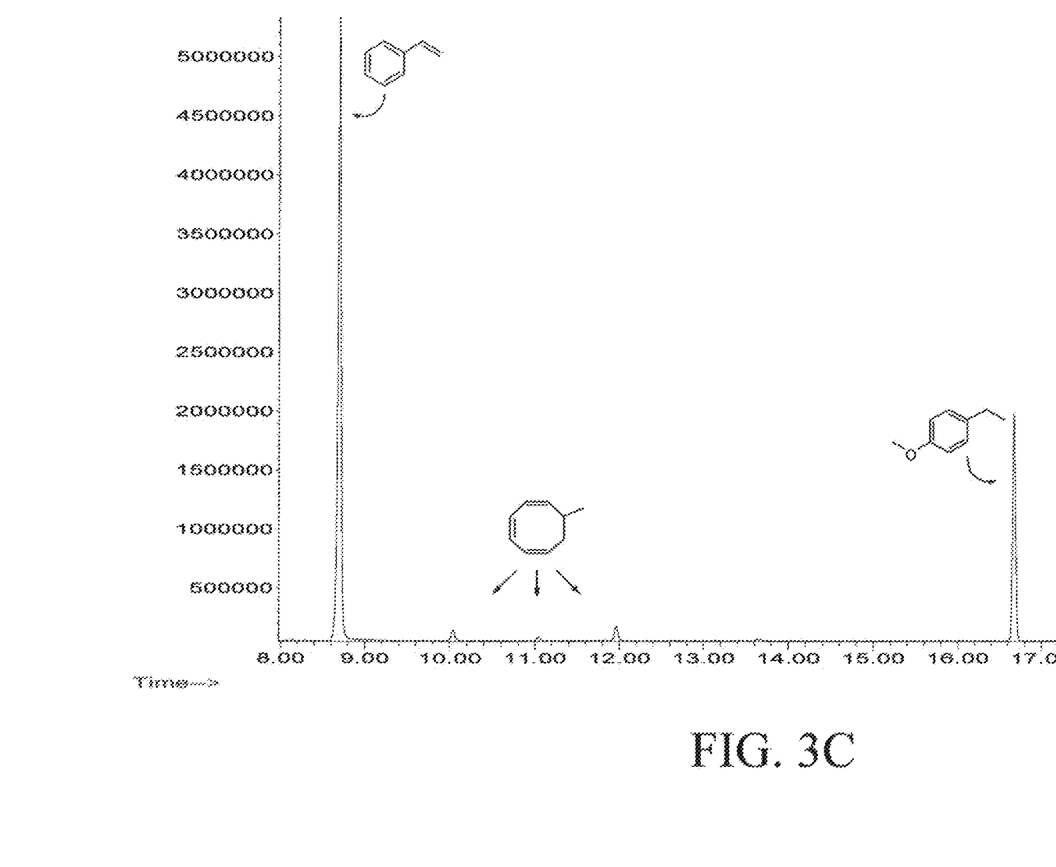

FIG. 3 shows representative traces of VOCs from a fungal bouquet on almonds; a fungal bouquet on PDA; and isolated fungus *F. oxysporum* strain on PDA.

Fungal isolates were identified by DNA sequence analysis of a portion of the 26S ribosomal RNA (rRNA) gene. For DNA extraction, fungi were grown in 10 mL of potato dextrose broth for 4 days at $28°$ C. without shaking. Mycelial mats were recovered by vacuum filtration onto Whatman No. 4 filter paper, frozen in liquid nitrogen and ground to a fine powder using a mortar and pestle. Ground mycelium was stored at $-80°$ C. until use. DNA from each sample was isolated using an adaptation of the method described in the literature (see e.g., Plaza, G. A., et al. (2004) *Polish J. Environ. Stud.* 2004, 13, 315-318). Briefly, approximately 500 mg of frozen powdered mycelium were added to 1 mL of lysis solution (0.1 M NaCl, 0.5 M Tris-Cl, pH 8.0, 5% SDS) and vortexed for 5 minutes. Cell debris was removed by centrifugation for 10 min. Aliquots of 500 µL from each sample were removed to a clean microfuge tube. Samples were extracted once with an equal volume of phenol-chloroform-isoamyl alcohol (25:24:1) and once with an equal volume of chloroform-isoamyl alcohol (24:1). DNA was precipitated by adding 2 volumes of cold isopropanol, mixing by inversion, and centrifuging for 10 min. Pellets were air-dried and re-dissolved in 100 µL of TE (10 mM Tris, pH 8.0, 1 mM EDTA, pH 8.0) containing 10 µg/mL RNAse.

The 26S rRNA gene fragment used for sequence analysis was amplified by polymerase chain reaction (PCR). Each reaction contained 0.3 µM each of primers NL-1 (5'-GCATATCAATAAGCGGAGGAAAAG-3' SEQ ID NO:1)

and NL-4 (5'-GGTCCGTGTTTCAAGACGG-3'SEQ ID NO:2) (see e.g., Kurtzman, C. P. and Robnett, C. J. (1998) Identification and phylogeny of ascomycetous yeasts from analysis of nuclear large subunit (26S) ribosomal DNA partial sequences. *Antonie Van Leeuwenhoek*, 73, 331-371) and 1 µL of fungal DNA. Amplified fragments were purified using the QIAquick PCR purification kit (Qiagen, Valencia Calif.). Sequencing was performed using the BigDye Terminator v. 3.1 Cycle Sequencing kit (Applied Biosystems, Foster City, Calif.) according to the manufacturer's suggestions, and run on an Applied Biosystems 3130×1 Genetic Analyzer. Sequences were assembled using Lasergene software (DNASTAR, Inc., Madison, Wis.) and sequence similarities were performed by BLAST search (see e.g., Altschul et al., Nuc. Acids Res. 25:3389-3402 (1977) and Altschul et al., J. Mol. Biol. 215:403-410 (1990)). Sequence similarities indicated that I3-4, I3-5 and I3-8 were isolates of *Fusarium oxysporum*.

Example 2

The following example illustrates that not all fungal isolates produce styrene.

Almond washes from previously treated almond hulls as disclosed in Example 1 were inoculated onto potato dextrose agar (PDA) for cultivation of fungal populations. From fungal populations (mixed cultures) that produced styrene individual fungal colonies were isolated by spreading 100 µL of the corresponding almond wash onto Dichloran-Rose Bengal-Chloramphenicol agar and incubated for 2 days at 28° C. Pure cultures of individual fungal isolates were inoculated onto PDA in 25 mL screw-top Erlenmeyer flasks and incubated for 6 days loosely capped. Caps were tightened for 1 day prior to VOC analyses as described in Example 1.

Twelve of fifteen fungal isolates produced isolable amounts of styrene under these conditions, of which six fungal isolates also produced MCOT in 1:3 to 1:5 ratios of MCOT to styrene. Visual inspection suggested fourteen of the fifteen fungal isolates were within the genus *Fusarium*. The remaining isolate exhibited a different growth color suggesting a *Penicillium* species. The putative *Penicillium* isolate produced styrene, only.

Example 3

The following example illustrates an exemplary small scale method for the capture and separation of volatile organic compounds (VOCs) from a culture of microorganisms capable of producing isolable amounts of styrene and/or 7-methyl-1,3,5-cyclooctatriene (MCOT). The Example also illustrates an exemplary pattern of biosynthesis of styrene and MCOT over time.

Isolates from Example 1, were inoculated into PDA in Teflon capped 25 ml Erlemmeyer flasks. VOCs were allowed to accumulate for 24 h sans air flow prior to exposure to SPME fibers. VOCs were immediately thermally desorbed onto the GC-MS injector port (Permeation of VOCs in collection chamber=24 h; Exposure of VOCs to SPME fiber=30 sec; Storage of VOCs on fiber=10 sec; Thermal desorbtion of VOCs=15 min). VOC samples were collected in duplicate and each sample separated and identified utilizing two different GC methods as described below.

Volatile organic compounds (VOCs) were collected onto solid phase microextraction (SPME) 100 µm polydimethylsiloxane (PDMS) fibers (Supelco, catalog #504823, Bellefonte, Pa.). SPME fibers were conditioned via the manufacturer's suggested protocol prior to use. VOCs were desorbed, separated, and identified using either a Hewlett Packard (HP) 6890 Series gas chromatogram (GC) coupled to HP 5973 mass selective detector (MS) (Hewlett-Packard, Palo Alto, Calif.), or an Agilent Technologies 6890N GC coupled to a 5975B inert MS (Santa Clara, Calif.). DB-Wax (60 m, 0.320 mm I.D., 0.25 µm film, catalog #123-7062) and DB-1 (60 m, 0.320 mm I.D., 0.25 µm film, catalog #123-1062) GC columns were purchased from Agilent J&W Scientific (Santa Clara, Calif.) and conditioned via the manufacturer's suggested protocol prior to use. Tenax was purchased from Chromatography Research Supplies, Inc. (Addison, Ill.) and conditioned with a helium flow (20 mL/min) while at 250° C. for 12 h. Diethyl ether (ACS grade), methanol (HPLC grade), n-pentane (HPLC grade), phenol, chloroform, isopropanol, TE solution, and lysis solution components were purchased from Fisher Scientific (Pittsburgh, Pa., and Fair Lawn, N.J.). Potato dextrose broth and agar were purchased from Becton, Dickinson & Company (Franklin Lakes, N.J.). Diethyl ether was treated with ferrous sulfate, dried over sodium sulfate, and distilled over ethanox 330 prior to use. Methanol and n-Pentane were used without further purification. Styrene for comparison of retention times, RNAse, isoamyl alcohol, and chloramphenicol were purchased from Aldrich (St. Louis, Mo., and Milwaukee, Wis.) and analyzed/used without further purification. SPME sampling was performed via the PEST method.[1] Semi-preparative high performance liquid chromatography (HPLC) was performed on a Hewlett-Packard 1100 Series HPLC with fluorescence detector (Hewlett-Packard, Palo Alto, Calif.), using a YMC-Pack Pro C18 (250× 10 mm, 5 µm, 12 nm) reversed-phase column (Supelco, Bellefonte, Pa.). Almonds, nonpareil variety, were obtained from Paramount Farming Company (Bakersfield, Calif.).

Small scale cultures were monitored over time to examine the pattern of VOC production.

Utilizing the 25 mL Erlenmeyer's containing inoculated PDA, the VOC emission was sampled by SPME every 24 h and analyzed by a rapid ramp GC-MS program. The graph in FIG. 3 shows the relative abundance of styrene versus time. Styrene was essentially the only component generated for three days. After eight days, a second component was produced in concurrence with a reduction of styrene production. The second volatile was identified as an isomer of MCOT.

Example 4

The following example illustrates an exemplary large scale method for the capture of volatile organic compounds from a culture of microorganisms capable of producing isolable amounts of styrene and/or 7-methyl-1,3,5-cyclooctatriene (MCOT). The Example also illustrates an exemplary pattern of biosynthesis of styrene and MCOT over time.

*Fusarium oxysporum* isolates from Example 1, were inoculated into a 12 L round bottom flask (RBF), charged with 1 L of potato dextrose broth (PDB). The inoculated culture was kept static and at room temperature for a total of 1,582 h. The experimental conditions for the inoculated broth scale-up were similar to a published method (see e.g., Hebbar, K. P, et al. (1997) *Appl. Microbiol. Biotechnol.* 48: 714-719). The RBF was attached to a metal cap, with Teflon gaskets, and two ports, one for purified air input (6 mL/min) and one for VOC collection onto a Tenax column (25 g in a 3×20 cm glass tube fitted with a fritted filter). Aluminum foil was wrapped around the Tenax collection column. Occasional VOC analysis, and relative styrene ratio determination, was accomplished by shutting off air flow to the RBF for 3 minutes, removing the air flow line, sampling with SPME (P=3 min; E=1 min; S=30 sec; T=15 min), and analyzing by GC-MS. A total of five Tenax columns were used for VOC collection: column 1, day 0 to day 3 (69.7 h); column 2, day 3 to day 7 (97.3 h, 167.0 h); column 3, day 7 to day 24 (405.9 h, 572.9 h); column 4 (2×10 g Tenax columns in tandem), day 24 to day 45 (509.6 h, 1082.5 h); column 5, day 45 to day 66 (499.3 h, 1581.8 h). Absorbed volatiles were desorbed from the Tenax via published protocol (see e.g., Beck, J. J., et al. (2008). J. Sci. Food. Agric. 88: 1363-1368). Briefly, the Tenax medium was washed with n-pentane, and the n-pentane concentrated via immersion of the RBF in a warm water bath and the n-pentane distilled until a mother liquor volume of ca. 100 mL.

Figure 4:
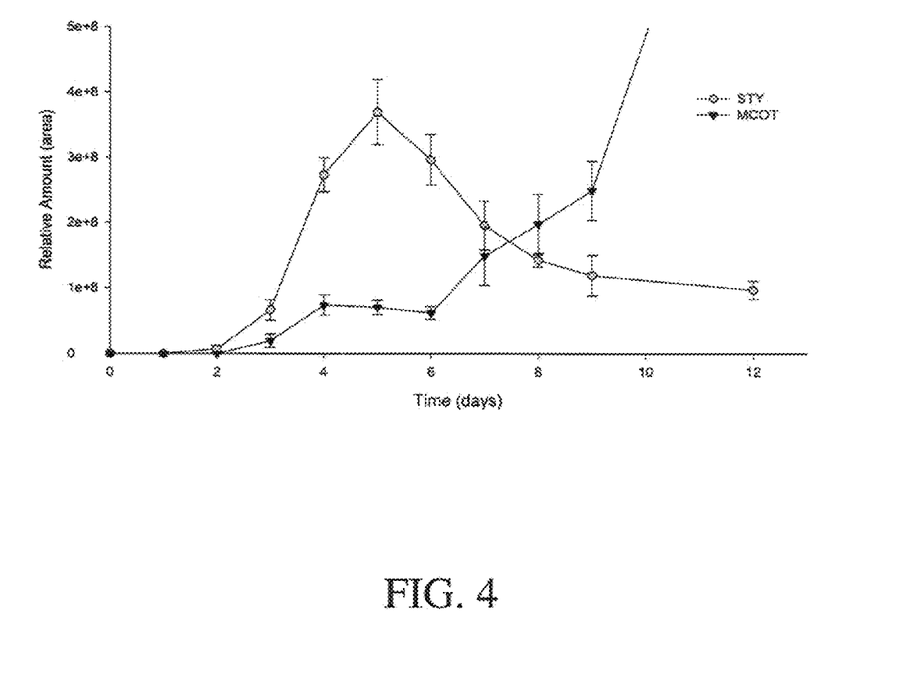
Figure 5:
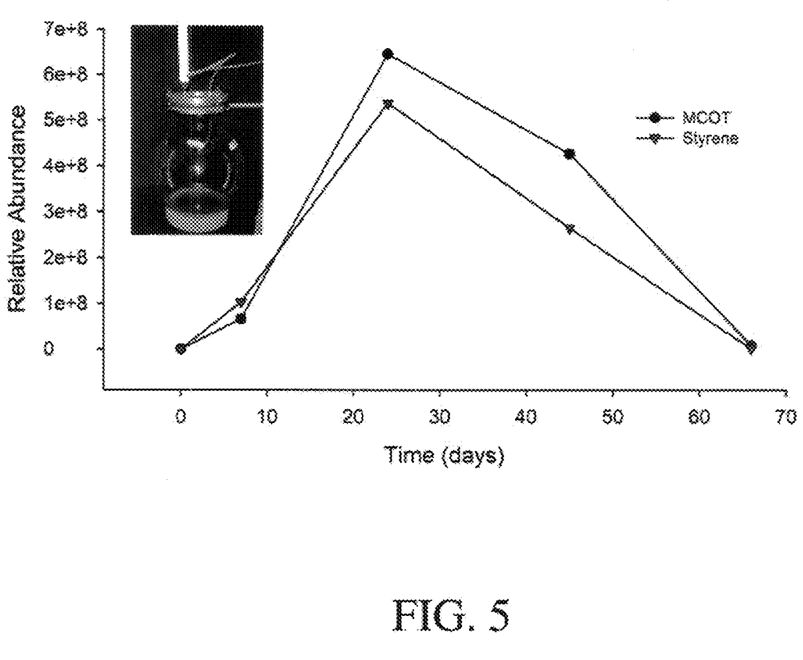
FIG. 5. Relative abundance of large scale styrene and MCOT production from *F. oxysporum* over a 66 day period. Chamber used to grow *F. oxysporum* on a larger scale (inset).

The VOC composition was occasionally monitored for relative abundance of styrene and MCOT (FIG. 4). For the first eleven days of VOC emission the large scale essentially mimicked the small scale relative amounts of styrene and MCOT, with styrene being in greater quantities; however, after eleven days MCOT exceeded and stayed above the amount of styrene generated. Near the time of VOC composition check near day 22, it appeared as if either the feedstock had started to run out, or the fungus had reached the peak of its ability to generate the two compounds. It was later determined that glucose levels can positively influence styrene production.

The volatiles were collected on a total of 5 Tenax "fractions"; the first cut, 0 to 3 days, coincided with days that no VOCs were generated. Although the small scale VOC collection experiment showed VOC production started on the third day large scale cultures did not start generating styrene until day six.

The second fraction, 3 to 7 days, was subjected to the usual method of desorbtion from the Tenax (23) and used for HPLC method development. For "Fraction 2", diethyl ether was used to desorb the volatiles from the Tenax. Unfortunately, when the ether mixture of Fraction 2 was concentrated for semi-preparative HPLC, the mixture underwent decomposition (the peak corresponding to styrene decreased over time). The cause of the decomposition was not determined. The information regarding the inability to concentrate the styrene mixture was however, duly noted and the VOCs from the Fraction 3 were desorbed using pentane and kept dilute prior to injection on the HPLC.

Example 5

The following example illustrates an exemplary method for the isolation of styrene from large scale culture.

Mother liquor from Example 4, was used to isolate styrene Aliquots (100 μL) of the mother liquor were separated via HPLC: 80:20, MeOH/H$_2$O; flow, 1.5 mL/min; pressure, 70-72 bar; detector, excitation 285 nm, emission 385 nm. Commercial styrene was used to determine the retention time of the peak to collect. Pure styrene, elution time 20.8 min, was collected into a darkened vial and stored in a refrigerator. Combined styrene fractions (ca. 10 runs) were transferred to a separatory funnel and chilled pentane (10 mL) added. The aqueous methanol layer was partitioned then washed twice more with chilled pentane (2×10 mL). The combined organic layers were dried over anhydrous sodium sulfate and concentrated in vacuo to a volume of approximately 0.5 mL (composition checked by GC-MS injection, 1 μL), and then a stream of nitrogen gas passed over the vial to near dryness to afford pure styrene (1.7 mg), confirmed by SPME and GC-MS analysis, which matched all data of authentic sample.

The total amount of styrene present in the 1 L culture was estimated by retracing the amount of styrene isolated against the relative abundances from the SPME and GC-MS (FIG. 4). According to the calculations approximately of 200-240 mg of styrene was generated from 1 L of inoculated broth over 66 days. This calculation does not include any styrene that may have been in the aqueous broth. If the solubility of styrene in water (300 mg/L) (31) is taken at face value, ignoring the fungus and by-products in the mixture, it is estimated that an additional 300 mg of styrene could have been present.

Example 6

The following example illustrates an exemplary method for the isolation of MCOT from large scale culture.

Aliquots (900 μL) of the mother liquor were separated via HPLC: 80:20, MeOH/H$_2$O 0-28.99 min; flow, 1.5 mL/min, then 99:1, MeOH/H$_2$O 29-42 min; flow, 2.0 mL/min; excitation 295 nm, emission 395 nm. SPME headspace GC-MS was used to determine the retention time of the peak to collect. MCOT isomers, elution time 38.5 min, were collected into a darkened vial and stored in a refrigerator. Combined fractions (ca. 7 runs) were transferred to a separatory funnel and chilled pentane (10 mL) added. The aqueous methanol layer was partitioned then washed twice more with chilled pentane (2×10 mL). The combined organic layers were dried over anhydrous sodium sulfate prior to concentration via gentle distillation in a warm water bath. Attempts to concentrate to neat MCOT resulted in complete loss of product. Ultimately, characterization was performed via MS fragmentation patterns and high-resolution MS (HRMS) with MCOT concentrated in pentane. Electron impact mass spectrum (EIMS 70 eV) found: 51 (10), 52 (9), 78 (100), 79 (20), 91 (20), 105 (15), 120 (9); HREIMS m/z 120.0941 (calcd for C$_9$H$_{12}$ 120.0939).

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A pilot or industrial scale biosynthetic method for preparing purified styrene, the method comprising:
   (i) culturing *Fusarium oxysporum* strain I3-8 deposited with the Agricultural Research Service Culture Collection (NRRL), and assigned Accession No. NRRL 50189, thereby providing a culture of the *Fusarium oxysporum* strain I3-8 assigned Accession No. NRRL 50189, wherein a gas chromatographic (GC) analysis which provides a GC trace reflective of the composition of the volatile organic compounds produced by the culture of the *Fusarium oxysporum* strain I3-8 assigned Accession No. NRRL 50189, indicates that styrene is at least one of the major peaks displayed in the GC trace;
   (ii) capturing volatile organic compounds produced by the culture of the *Fusarium oxysporum* strain I3-8 assigned Accession No. NRRL 50189 thereby providing a mixture of captured volatile organic compounds;
   (iii) separating the captured mixture of volatile organic compounds into individual volatile organic compounds;
   (v) identifying styrene; and
   (vi) collecting the identified styrene as purified styrene.

2. The method of claim 1, wherein capturing volatile organic compounds produced by the culture of the *Fusarium oxysporum* strain I3-8 assigned Accession No. NRRL 50189 comprises:
   a. condensing volatile organic compounds produced by the culture of the *Fusarium oxysporum* strain I3-8 assigned Accession No. NRRL 50189 to provide a condensate comprising a mixture of volatile organic compounds;
   b. collecting the condensate thereby providing a captured mixture of volatile organic compounds; and
   c. distilling the condensate to separate the mixture of volatile organic compounds into individual volatile organic compounds.

3. The method of claim 1, wherein collecting the identified styrene comprises:
   a. polymerizing styrene produced by the microorganism culture.

4. The method of claim 1, wherein capturing volatile organic compounds produced by the culture of the *Fusarium oxysporum* strain I3-8 assigned Accession No. NRRL 50189 comprises:
   (a) adsorbing volatile organic compounds produced by the culture of the *Fusarium oxysporum* strain I3-8 assigned Accession No. NRRL 50189 on a porous polymer absorption column, thereby providing a mixture of absorbed volatile organic compounds; and
   (b) desorbing the mixture of adsorbed volatile organic compounds with an appropriate solvent, thereby providing a captured mixture of volatile organic compounds.

5. The method of claim 4, wherein the appropriate solvent is a non-polar solvent.

6. The method of claim 5, wherein the non-polar solvent is n-pentane.

7. The method of claim 1, wherein the method is practiced on an industrial scale.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: 26S Ribosomal RNA

<400> SEQUENCE: 1
gcatatcaat aagcggagga aaag                                              24

```
<210> SEQ ID NO 2
<211> LENGTH: 19
<212> TYPE: DNA
<213> ORGANISM: Artificial
<220> FEATURE:
<223> OTHER INFORMATION: 26S Ribosomal RNA

<400> SEQUENCE: 2
ggtccgtgtt tcaagacgg                                                  19
```